US008066744B2

(12) United States Patent  
Justis et al.

(10) Patent No.: US 8,066,744 B2
(45) Date of Patent: Nov. 29, 2011

(54) KEYED CROWN ORIENTATION FOR MULTI-AXIAL SCREWS

(75) Inventors: Jeff R. Justis, Germantown, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 945 days.

(21) Appl. No.: 11/558,739

(22) Filed: Nov. 10, 2006

(65) Prior Publication Data

US 2008/0114362 A1    May 15, 2008

(51) Int. Cl.
*A61B 17/70* (2006.01)
(52) U.S. Cl. ......... 606/266; 606/246; 606/286; 606/305
(58) Field of Classification Search .......... 606/60, 606/246–279
See application file for complete search history.

(56) References Cited

U.S. PATENT DOCUMENTS

| 6,440,137 B1 * | 8/2002 | Horvath et al. ............ 606/302 |
| 6,478,798 B1 | 11/2002 | Howland |
| 6,485,491 B1 | 11/2002 | Farris et al. |
| 6,547,790 B2 | 4/2003 | Harkey, III et al. |
| 6,626,906 B1 | 9/2003 | Young |
| 6,652,526 B1 * | 11/2003 | Arafiles ..................... 606/308 |
| 6,770,075 B2 | 8/2004 | Howland |
| 6,802,844 B2 | 10/2004 | Ferree |
| 6,896,677 B1 * | 5/2005 | Lin ............................ 606/266 |
| 2001/0001119 A1 * | 5/2001 | Lombardo ................. 606/73 |
| 2003/0125741 A1 | 7/2003 | Biedermann et al. |
| 2004/0176766 A1 | 9/2004 | Shluzas |
| 2004/0186478 A1 * | 9/2004 | Jackson .................... 606/73 |
| 2004/0215190 A1 * | 10/2004 | Nguyen et al. ............ 606/61 |
| 2004/0249380 A1 | 12/2004 | Glascott |
| 2004/0267264 A1 * | 12/2004 | Konieczynski et al. ... 606/73 |
| 2005/0049589 A1 * | 3/2005 | Jackson .................... 606/61 |
| 2005/0261687 A1 | 11/2005 | Garamszegi et al. |
| 2005/0277928 A1 * | 12/2005 | Boschert .................. 606/61 |
| 2006/0200131 A1 * | 9/2006 | Chao et al. ............... 606/61 |
| 2006/0217716 A1 * | 9/2006 | Baker et al. .............. 606/61 |
| 2006/0264933 A1 * | 11/2006 | Baker et al. .............. 606/61 |
| 2006/0276789 A1 * | 12/2006 | Jackson .................... 606/61 |

FOREIGN PATENT DOCUMENTS

| DE | 44 25 357 A1 | 2/1996 |
| EP | 1604617 A1 * | 12/2005 |
| FR | 2 794 637 A1 | 12/2000 |
| WO | 03/068083 A | 8/2003 |
| WO | WO 2004107997 A2 * | 12/2004 |
| WO | 2005/102195 A | 11/2005 |

OTHER PUBLICATIONS

European Patent Office, "Notification of Transmittal of the International Search Report and The Written Opinion of the International Searching Authority, or the Declaration," for PCT/US2007/083296, mailed Apr. 11, 2008, 15 pages.

(Continued)

*Primary Examiner* — Eduardo C Robert
*Assistant Examiner* — Jerry Cumberledge (57) ABSTRACT

A coupling assembly may include an anchor member, a receiver member, and a seat member. The receiver member may have an anchor member end that cooperates with the anchor member and may have an implant receiving aperture for receiving an implant. The seat member may be disposable within the receiver member between the anchor member and the implant receiving aperture. First and second rotation-limiting features may be engageable to limit rotation of the seat member relative to the receiver member.

28 Claims, 7 Drawing Sheets

OTHER PUBLICATIONS

Unpublished U.S. Appl. No. 11/112,221, filed Apr. 22, 2005, titled "Force Limiting Coupling Assemblies for Spinal Implants".

Unpublished U.S. Appl. No. 11/197,779, filed Aug. 5, 2005, titled "Coupling Assemblies for Spinal Implants".

* cited by examiner

KEYED CROWN ORIENTATION FOR MULTI-AXIAL SCREWS

BACKGROUND

The present disclosure generally relates to orthopedic coupling assemblies for anchors used with implants for correction of spinal injuries or deformities.

In the realm of orthopedic surgery, implant systems may be utilized to fix the position of bones. In this way, the healing of a broken bone can be promoted, and malformations or other injuries can be corrected. Typical implant systems include several pieces. Bone screws, for example, are well know as fixation devices, which are connected or adjoined to a particular bone as a connection between the remainder of the implant and the bone. With rod-type implants, a series of two or more screws are typically inserted into two or more vertebrae to be instrumented. The rod is then placed within or coupled to the heads of the screws, or is placed within a connecting device that links the rod and a screw head, and the connections are tightened. In this way, a rigid supporting structure is fixed to the vertebrae, with the rod providing the support that promotes correction of the vertebral malformation or injury.

Multi-axial bone screws often have multiple pieces, allowing a threaded portion to engage the bone and a head portion to connect to the remaining implant system, such as the rod. Other components engage, hold, attach to, or affect the movement of the rod relative to the screw. Alignment of these components can be difficult and tedious within the confines of a surgical opening. Accordingly, what is needed is a screw that allows simple securing of screw components in a desired position.

SUMMARY OF THE INVENTION

In one exemplary aspect, the present disclosure is directed to a coupling assembly including anchor member and a receiver member. The receiver member may have an anchor member end that cooperates with the anchor member and may have an implant receiving aperture for receiving an implant. The receiver member may have a shaped inner surface forming a first rotation-limiting feature. A seat member may be disposable within the receiver member between the anchor member and the implant receiving aperture, and may have a shaped outer surface forming a second rotation-limiting feature. The first and second rotation-limiting features may be engageable to limit rotation of the seat member relative to the receiver member.

In another exemplary aspect, the present disclosure is directed to a coupling assembly including an anchor member and a receiver member. The receiver member may have an anchor member end cooperating with the anchor member and may have an implant receiving aperture for receiving an implant. The receiver member may have an annular inner surface portion. A seat member may be disposable within the receiver member between the anchor member and the implant receiving aperture. The seat member may have an annular outer peripheral surface portion. The annular inner surface portion and the outer annular peripheral surface portion may be engageable to limit rotation of the seat member relative to the receiver member.

In yet another exemplary aspect, the present disclosure is directed to a method of assembling a coupling assembly for securing an implant. The method may include introducing a seat member into a receiver member. The receiver may have an anchor member end configured to cooperate with an anchor member and may have an implant receiving aperture for receiving an implant. The method also may include limiting rotation of the seat member relative to the receiver member by engaging a shaped inner surface of the receiver member forming a first rotation-limiting feature with a shaped outer surface of the seat member forming a second rotation-limiting feature.

In yet another exemplary aspect, the present disclosure is directed to a coupling assembly including an anchor member and a receiver member. The receiver member may have an anchor member end that cooperates with the anchor member and an implant receiving aperture for receiving an implant. The receiver member may include an inner surface and a first rotation-limiting feature associated with the inner surface. A seat member may be disposable within the receiver member between the anchor member and the implant receiving aperture. The seat member may include an outer surface and a second rotation-limiting feature associated with the outer surface. One of the first and second rotation limiting features may be sized with a width greater than a width of the other of the first and second rotation limiting features. The first and second rotation-limiting features may be engageable to limit rotation of the seat member relative to the receiver member.

In another exemplary aspect, the present disclosure is directed to a coupling assembly including an anchor member and a receiver member. The receiver member may have an anchor member end that cooperates with the anchor member and an implant receiving aperture for receiving an implant. The receiver member may include an inner surface and a first rotation-limiting feature associated with the inner surface. A seat member may be disposable within the receiver member between the anchor member and the implant receiving aperture. The seat member may include an outer surface and a second rotation-limiting feature associated with the outer surface. The first and second rotation-limiting features may be engageable to permit a limited degree of rotation of the seat member relative to the implant receiver member.

In yet another exemplary aspect, the present disclosure is directed to a coupling assembly including an anchor member and a receiver member. The receiver member may have an anchor member end that cooperates with the anchor member and an implant receiving aperture for receiving an implant. The receiver member may include an inner surface and a first rotation-limiting feature associated with the inner surface. A seat member may be disposable within the receiver member between the anchor member and the implant receiving aperture. The seat member may include an outer surface and a second rotation-limiting feature associated with the outer surface. One of the first and second rotation limiting features may include a plurality of positions shaped to cooperate with the other of the first and second rotation limiting features in a manner that permits selective engagement of one of the plurality of positions with the other of the first and second rotation limiting features to limit rotation of the seat member relative to the receiver member.

In yet another exemplary aspect, the present disclosure is directed to a coupling assembly including an anchor member and a receiver member. The receiver member may have an anchor member end that cooperates with the anchor member and may have an implant receiving aperture for receiving an implant. A seat member may be disposable within the receiver member between the anchor member and the implant receiving aperture. The seat member may include an outer surface and a rotation-limiting feature associated with the outer surface. A rotation limiter may be configured to engage the rotation limiting feature of the seat member through the implant receiving aperture.

DETAILED DESCRIPTION

The present invention relates generally to coupling assemblies for anchoring systems used for implantation of a vertebral device. For the purposes of promoting an understanding of the principles of the invention, reference will now be made to embodiments or examples illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Coupling assemblies typically include an anchor member for engaging the coupling assembly to an underlying bony structure, a receiver member for receiving the implant, and a securing member for securing the implant to the receiver member. The exemplary coupling assemblies disclosed herein also include a seat member in the receiver member located between the anchor member and the implant. The seat members shown each include rotation limiting features that help align the seat member with the receiver member.

Figures 1, 2, 3:
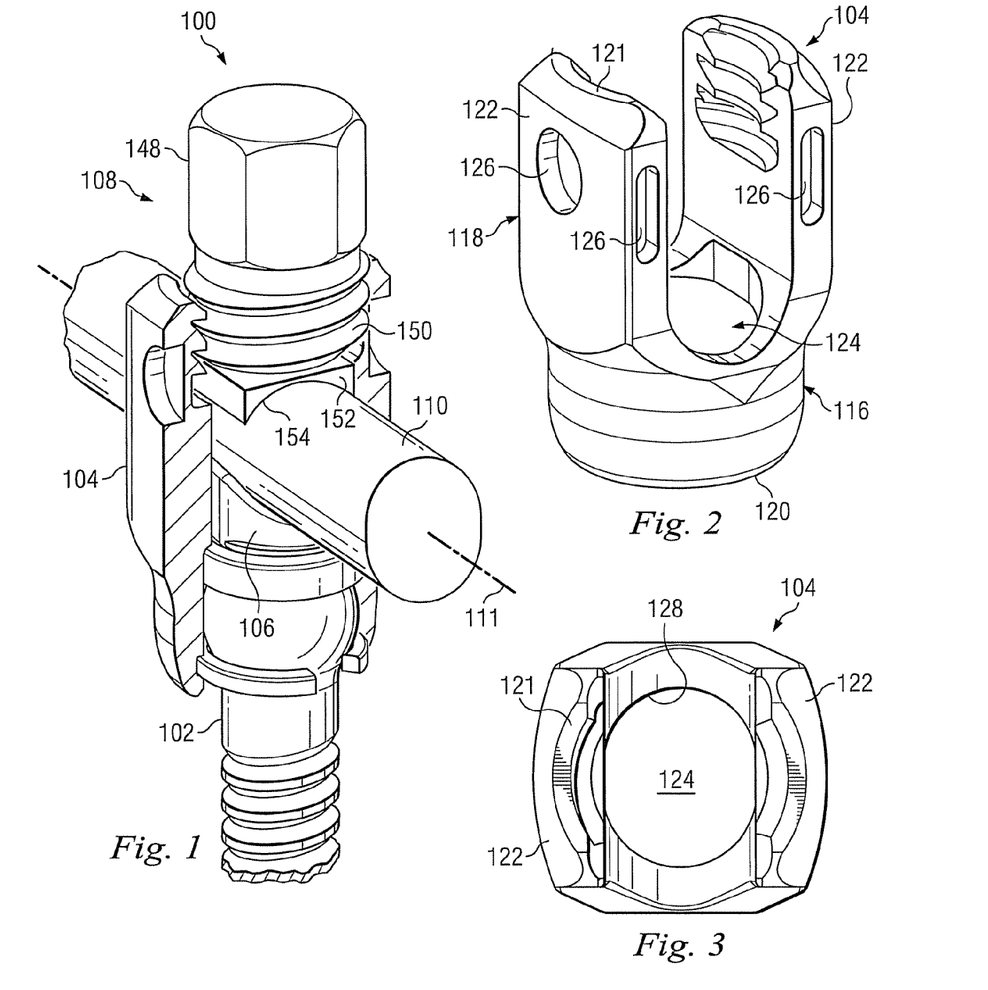
FIG. 1 is an illustration of a partial cross-sectional isometric view of an exemplary coupling assembly with an implant.
FIG. 2 is an illustration of an isometric view of an exemplary receiver member of the coupling assembly of FIG. 1.
FIG. 3 is an illustration of a top view of the receiver member of FIG. 2.

Turning now to FIG. 1, a coupling assembly 100 includes an anchor member 102, a receiver member 104 coupled to the anchor member 102, a crown or seat member 106, and a securing member 108. FIG. 1 also shows an implant 110 defining an implant axis 111 and extending through the receiver member 104 and held in place by the securing member 108. In use, the coupling assembly 100 is configured to secure the implant 110 in place relative to a spinal column.

The coupling assembly is described in greater detail with reference to FIGS. 2-7. Referring first to FIGS. 6 and 7, the anchor member 102 includes a head 112 and a threaded shaft portion 113. The head 112 is pivotally disposed within the receiver member 104 and retained in the receiver member 104 with a retaining clip 114. Other means for securing anchor member 102 in the receiver member 104 are also contemplated, including forming the lower opening of receiver member 104 to retain the head 112, providing retaining structures such as collars, washers, bushings, or other devices.

The receiver member 104, seen best in FIGS. 2 and 3 includes a lower portion 116 and an upper portion 118. In the embodiment shown, the head 112 of the anchor member 102 may be inserted into the receiver member 104 through an anchor cooperating end 120 at the lower portion 116 so that it is disposed within the lower portion 116. However, in other embodiments, the anchor member 102 is inserted through an upper end 121 at the upper end 118 and secured to the receiver member 104.

A pair of opposing arms 122 extend axially from opposite sides of the lower portion 116 to form a saddle arrangement to receive an implant, such as the implant 110 in FIG. 1, and engage the securing member 108. The seat member 106 may be positioned between the arms 124 adjacent the head 112 of the anchor member 102. The opposing arms 122 define an implant receiving aperture 124 therebetween that is sized to receive the implant 110. The arms 122 may each include an internal thread profile to threadingly engage the securing member 108, although other engagement structures to engage securing member 108 and receiver member 104 to one another are contemplated. The arms 122 also may include various geometries 126 to receive and facilitate engagement by and manipulation with insertion and/or reduction instrumentation (not shown.).

The lower portion of the receiver member 104 includes a rotation limiting feature 128 configured to cooperatively limit rotation of the seat member 106 within the receiver member 104. In the embodiment shown, the rotation limiting feature 128 is a shaped non-circular inner surface portion. The surface portion may be an oval-shape as shown or other non-circular shaped inner surface shaped to cooperate with an outer surface shape of the seat member 106.

Figure 4A:
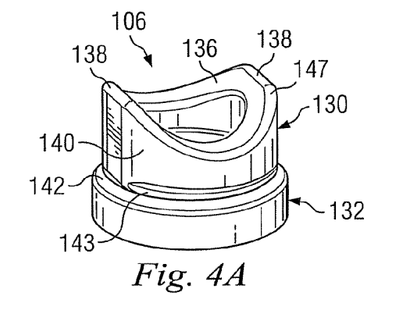
FIGS. 4A and 4B are illustrations of an isometric view and a top view respectively of an exemplary seat member of the coupling assembly of FIG. 1.
Figure 4B:
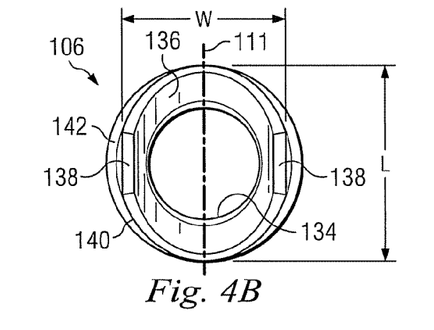
Figures 5, 6, 7:
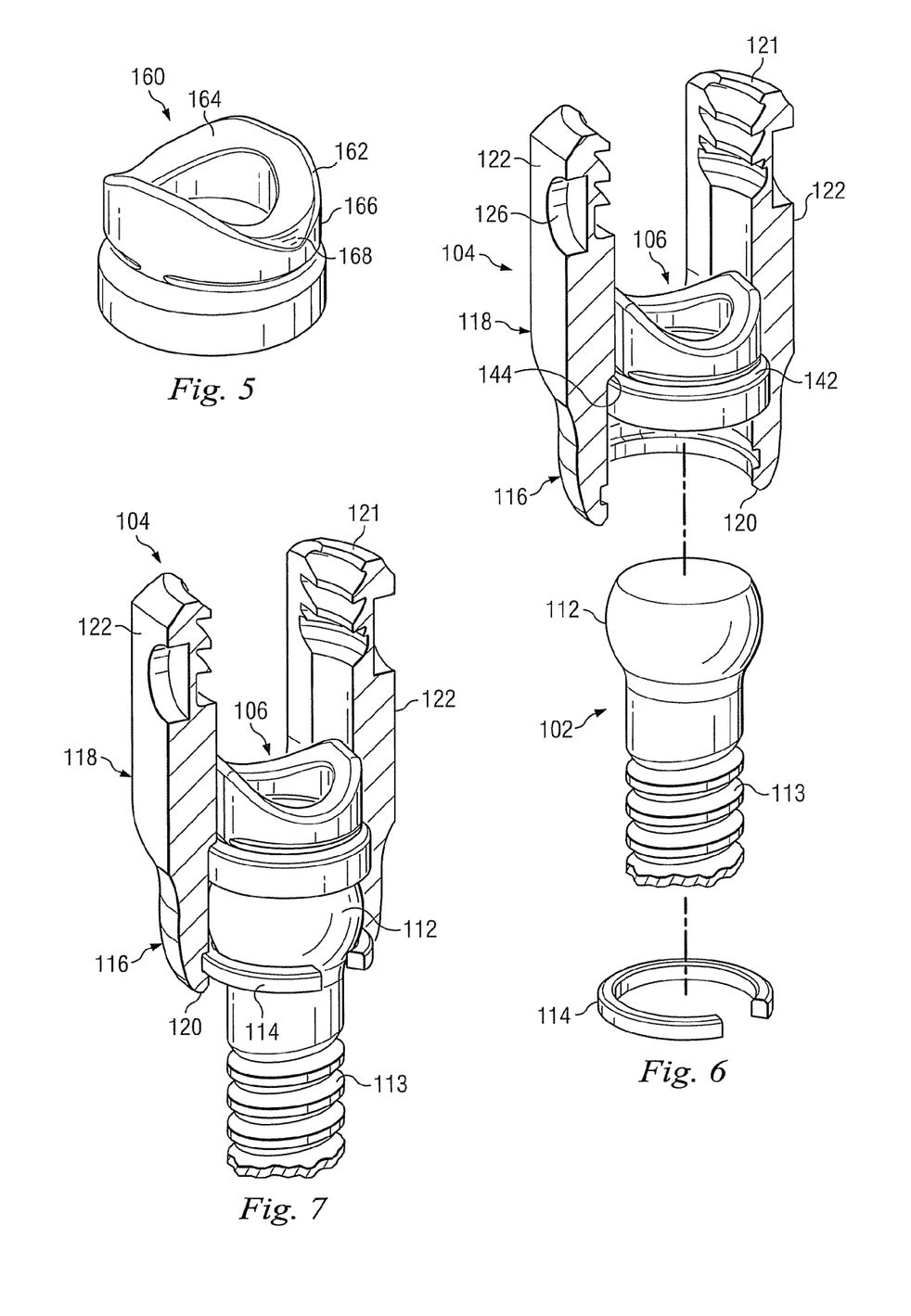
FIG. 5 is an illustration of an isometric view of an alternative exemplary seat member usable with the coupling assembly of FIG. 1.
FIG. 6 is an illustration of a partial cross-sectional of a partially exploded view of the coupling assembly of FIG. 1 without the securing member.
FIG. 7 is an illustration of a partial cross-sectional of the coupling assembly of FIG. 1 without the securing member.

Referring now to FIGS. 4A and 4B, the crown or seat member 106 includes an upper portion 130 and a lower portion 132 with a through-hole forming a central opening 134. The through hole is in communication with the head 112 of the anchor member 102 to receive a driving tool (not shown) to apply a driving force to the anchor member 102. The upper portion 130 of the seat member 106 includes a proximally oriented implant support surface 136 that together with the receiver member 104 may help define a lower or distal portion of the implant receiving aperture 124. The implant support surface 136 extends between proximal extensions 138, forming a proximally oriented U-shaped surface that is configured to be positioned substantially entirely in contact with the outer surface of the implant 110. In the illustrated embodiment, the implant support surface 136 is concavely curved, although non-curved shapes are also contemplated. The implant support surface 136 may be defined at least in part by the proximal extensions 138 of the seat member 106.

The upper portion 130 of the seat member 106 includes a rotation limiting feature 140 shaped to engage the rotation limiting feature 128 of the receiver member 104 to cooperatively limit rotation of the seat member 106 within the receiver member 104. In the embodiment shown, the rotation limiting feature 140 is a non-circular peripheral surface portion having a non-circular perimeter. The surface perimeter may be an oval-shape as shown or other non-circular shaped outer surface. For example, in some embodiments, the non-circular surface portion may be in the shape of a square, a rectangle, a hexagon, or other shape. In the embodiment shown, both the rotation limiting feature 128 of the receiver member 104 and the rotation limiting feature 140 of the seat member 106 are formed of smooth annular surfaces configured to mate and limit the ability of the seat member 106 to rotate relative to the receiver member 104.

As shown in FIG. 4B, the rotation limiting feature 140 includes a width W and a length L, with the length L being greater than the width W. In the embodiment shown, the length L is configured to align with the axis 111 of a received implant 110. In other embodiments employing a shaped surface portion as the rotation limiting feature the width and length may be similar, such as when the rotation limiting feature is a square shaped surface portion.

The lower portion 132 of the seat member 106 includes a circular peripheral surface portion having a circular perimeter that extends beyond the upper portion 130 forming a shoulder surface 142. This shoulder surface 142 may engage a corresponding shoulder 144 in the receiver member 104 to secure the seat member from passing though the receiver member 104 as shown in FIG. 6. An undercut 143 may be included between the upper and lower portions 130, 132 to help provide a suitable interface between the shoulder surfaces 142, 144. The lower portion 132 also may include a socket (not shown) in its bottom end 146 that pivotally receives the anchor member head 112.

In other contemplated embodiments, the rotation limiting feature 140 of the seat member 106 is shaped differently than the rotation limiting feature 128 of the receiver member 104. For example, the rotation limiting feature 140 may be a square-shaped surface perimeter and the rotation limiting feature 128 may be a rectangular-shaped surface. Other geometric shaped surfaces also are contemplated. These differently-shaped rotation limiting features still cooperate to limit rotational movement of the seat member 106 within the receiver member 104.

The implant support surface 136 and the perimeter surface of the upper portion 130 meet to form an edge 147. In the embodiment shown, the edge 147 extends around and includes a substantially constant radius of curvature.

FIG. 5 shows an alternative embodiment of a seat member 160 usable in the coupling assembly 100 in place of seat member 106. The seat member 160 may include the features of the seat member 106 described above, and may include an edge 162 between an implant support surface 164 and the outer perimeter surface of an upper portion 166. In the embodiment shown, the edge 162 includes a bull nose feature 168 that may provide a smooth engagement with the implant 110. The bull nose feature 168 may be an area of the edge 162 having a greater radius of curvature than other regions of the edge 162. In the embodiment shown, the bull nose feature is formed in the edge 162 in a region that would align with the axis 111 of the implant 110. In use, the gradual transition of the bull nose feature 168 may assist in force distribution on the implant 110. This may be particularly helpful when the implant is formed of a non-metal material, such as, for example, a polymer material.

Referring back to FIG. 1, the securing member 108 is movably engageable with the receiver member 104 to secure the implant 110 in engagement with the seat member 106. The securing member 108 may include a proximal break-off portion 148 and a receiver engaging portion 150, although embodiments without the break-off portion 148 are contemplated. The receiver engaging portion 150 is illustrated as an externally threaded set screw that engages the internal thread profile along the arms 122, although other configurations are contemplated.

The securing member 108 further comprises a distal implant engaging portion 152 that is mounted to and rotatable relative to engaging portion 150. In the illustrated embodiment, implant engaging portion 152 includes a concave surface 154 that engages the implant 110. As receiver engaging portion 150 is threadingly engaged along the arms 122, the distal implant engaging portion 152 can advance linearly toward the implant 110.

During assembly, the seat member 106 may be introduced to the receiver member 104 through the anchor cooperating end 120 of the lower portion 116. Because the rotation limiting features 128, 140 allow the seat member 106 to be disposed only in a proper orientation, introducing the receiver member 106 into the receiver member 104 may require aligning the rotation limiting features. The anchor member 102 is then introduced into the lower portion 106 through the anchor cooperating end 120 and secured in place with the clip 114. The seat member 106 is sized to axially slide within the receiver member 104 even when the rotation limiting features are engaged but this sliding is limited by the shoulders 142, 144 and the screw member 102.

In use, the anchor member 102 is engaged to an underlying bony structure with receiver member 104 positioned to receive the implant 110. The implant 110 is positioned in implant receiving aperture 124 of the receiver member 104 along or adjacent implant support surface 136 of the seat member 106. Because the seat member 106 and the receiver member 104 each include rotation limiting features, it is not necessary to align the implant support surface of the seat member 106 with the implant receiving aperture 124 of the receiver member 104 when connecting the receiver member 104 to the implant 110. The securing member 108 engages the receiver member 104, and advances there along until the implant engaging surface 152 contacts the implant 110. As the securing member 104 is further advanced distally in receiver member 104, the seat member 106 axially slides inside the receiver member 104 and the seat member 106 compression locks the head 112 of the anchor member 102 in a desired position, thereby securing the receiver member 104 in a fixed position relative to the anchor member 102. The implant engaging portion 152 is maintained in contact with the implant 110 while the receiver engaging portion 150 is threadingly engaged with receiver member 104 until sufficient resistance is encountered to sever the break-off portion 148.

Anchor member 102 in the illustrated embodiment is a bone screw including the shaft 113. However, various forms for anchor member 102 are contemplated, including threaded and non-threaded anchors, uni-axial and multi-axial arrangements, hooks, clamps, spikes, cables, interbody implants, fusion devices, non-cannulated screws, fenestrated screws, and bolts, for example.

Figure 8:
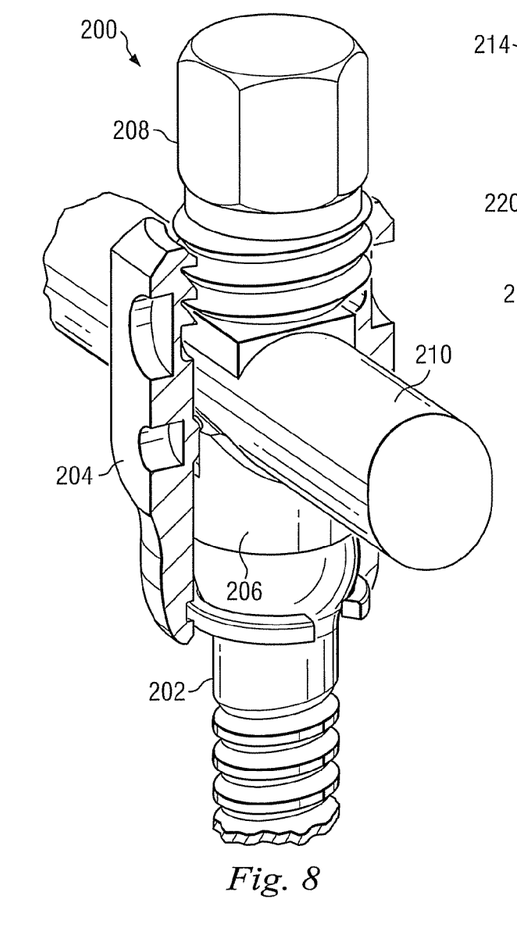
FIG. 8 is an illustration of a partial cross-sectional isometric view of another exemplary coupling assembly with an implant.

Turning now to FIGS. 8-14, another coupling assembly embodiment 200 is shown. As best seen in FIG. 8, the coupling assembly 200 includes an anchor member 202, a receiver member 204 coupled to the anchor member 202, a seat member 206, and a securing member 208. FIG. 8 also shows an implant 210 extending through the receiver member 204 and held in place by the securing member 208. In this embodiment, the anchor member 102 and the securing member 108 may be similar to those described above and are not described further here. Likewise, the receiver member 204 and the seat member 206 have many features similar to the receiver member 104 and the seat member 106 described above. To avoid repetition, some of these similarities are not again discussed here.

Figure 9:
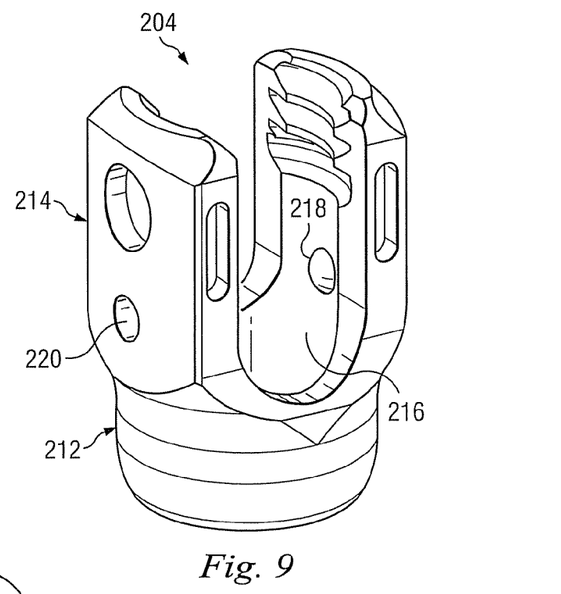
FIG. 9 is an illustration of an isometric view of an exemplary receiver member of the coupling assembly of FIG. 8.
Figure 10:
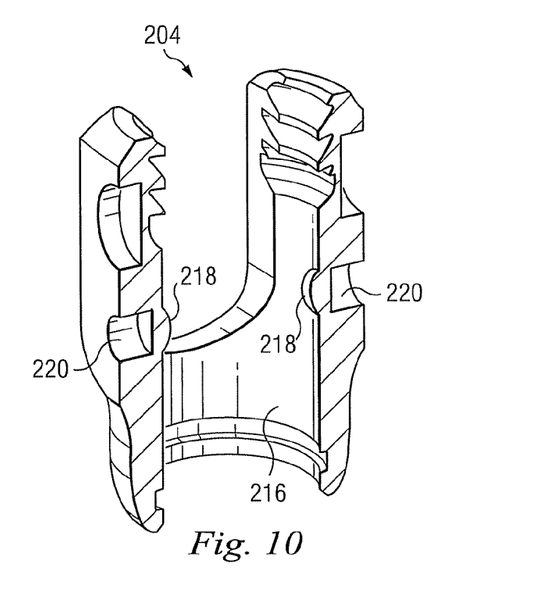
FIG. 10 is an illustration of a cross-sectional isometric view of the receiver member of FIG. 9.
Figure 11:
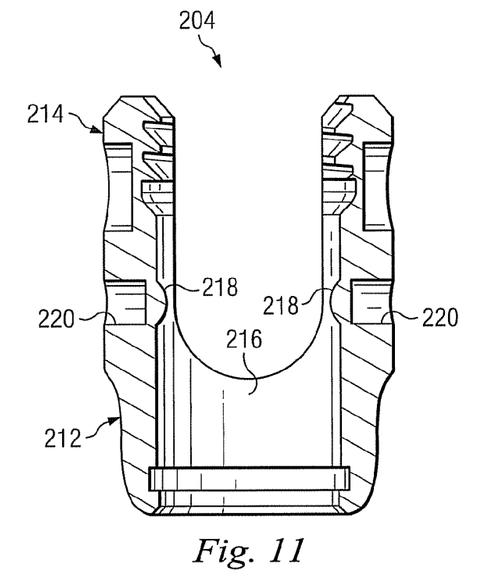
FIG. 11 is an illustration of a cross-sectional side view of the receiver member of FIG. 9.

Referring first to FIGS. 9-11, the receiver member 204 includes a lower portion 212, an upper portion 214, and an inner surface 216 extending through the lower and upper portions 212, 214. The inner surface 216 may form a circular interior. A rotation-limiting feature 218 is associated with and protrudes from the inner surface 216 of the receiver member 204. In the embodiment shown, the rotation-limiting feature 218 is a pre-formed protruding, semi-spherical dimple integrally formed with the receiver member during manufacturing. In other embodiments, the rotation limiting feature 218 is pre-formed and attached to the inner surface 216 prior to implantation. The rotation limiting feature 218 is shown in the upper portion 214 of the receiver member 204, but may alternatively be disposed along the inner surface 216 in the lower portion 212. In other embodiments, the rotation limiting feature 218 is a protruding feature formed as a cylinder, square, bump, or other shape. Adjacent the rotation limiting feature 218, extending inwardly from the exterior of the receiver member 204, lies a bore 220.

Figure 12:
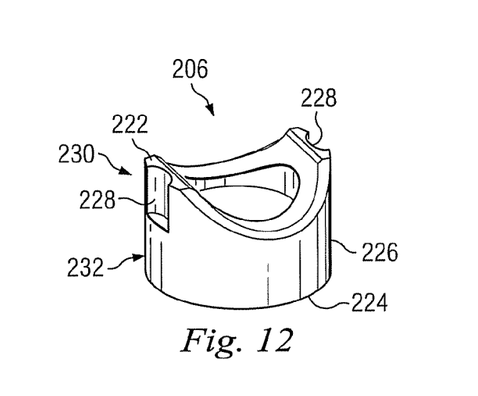
FIG. 12 is an illustration of an isometric view of an exemplary seat member of the coupling assembly of FIG. 8.
Figure 13:
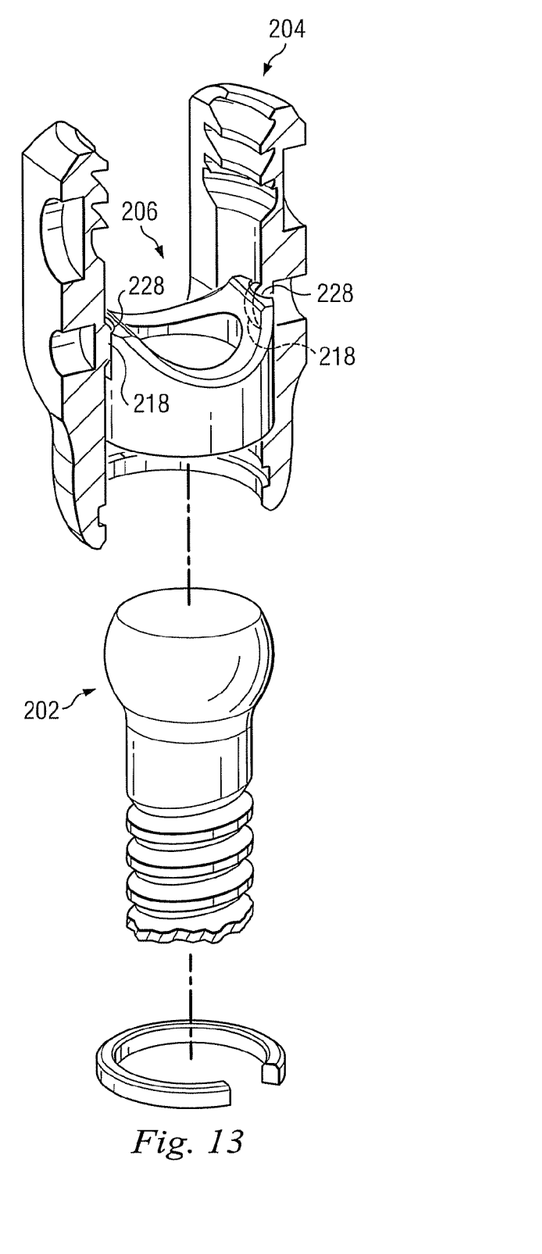
FIG. 13 is an illustration of a partial cross-sectional of a partially exploded view of the coupling assembly of FIG. 8 without the securing member.
Figure 14:
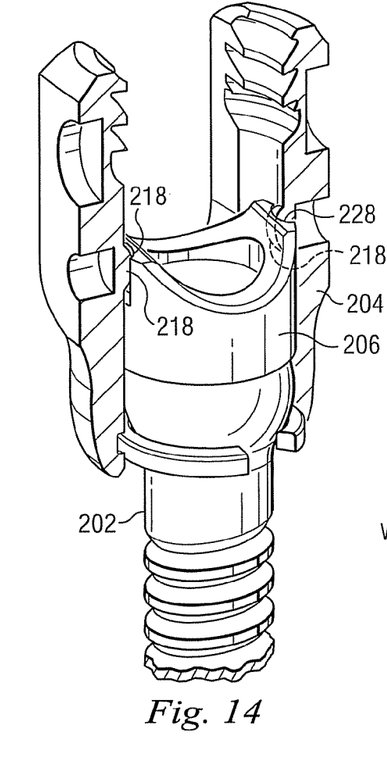
FIG. 14 is an illustration of a partial cross-sectional of the coupling assembly of FIG. 8 without the securing member.

As best seen in FIG. 12, the seat member 206 includes upper and lower ends 222, 224 respectively, and an outer surface 226 extending between the upper and lower ends 222, 224. The upper end 222 may include the implant support surface. The outer surface 226 in this embodiment has a diameter sized just less than the inner diameter of the receiver member 204 so that the seat member 206 may be received into the receiver member 204. A pre-formed rotation limiting feature 228 formed on an upper portion 230 of the receiver member 204 extends from the upper end 230 and ends at a lower portion 232 somewhere before the lower end 224. In this embodiment, the rotation limiting feature 228 is a concave semi-cylindrical recess having a size and shape that matches the profile of the semi-spherical shaped rotation limiting feature 218 on the receiver member 204 (best seen in FIG. 13). Accordingly, when the receiver member's rotation limiting feature 218 is engaged with the seat member's rotation limiting feature 228, the seat member 206 is unable to rotate within the receiver member 204. This may assist in properly aligning the receiving and seat members 204, 206 for proper securing of the implant 210. In addition, the length of the seat member's rotation limiting feature 228 is configured to allow the seat member 206 to slide axially within the receiver member 204, while still limiting any rotation. Although shown as being semi-cylindrical, the seat member's rotation limiting feature 228 may be configured otherwise to mate with the receiver member's rotation limiting feature 218 and/or match the shape of the receiver member's rotation limiting feature 218. In the embodiment shown, the receiver member 204 is shown with two opposing rotation limiting features 218 (best seen in FIG. 10), and the seat member 206 is shown with two opposing rotation limiting features 228 (best seen in FIG. 12). In other embodiments, one or both of the receiver member 204 and the seat member 206 may include a single rotation limiting feature, or alternatively, more than two rotation limiting features.

Assembling the coupling assembly 200 may follow substantially the same process described above with reference to the coupling assembly 100. The rotation limiting features 218, 228 allow the seat member 206 to be disposed only in a proper orientation. Axially sliding of the seat member is limited by the rotation limiting feature 228 and the lower portion of the seat member 206. Implantation and use also substantially follows a process similar to that described above.

Figure 15:
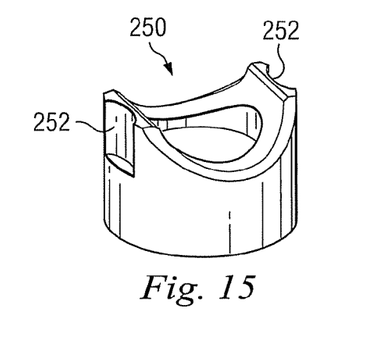
FIG. 15 is an illustration of an isometric view of another exemplary seat member.
Figure 16:
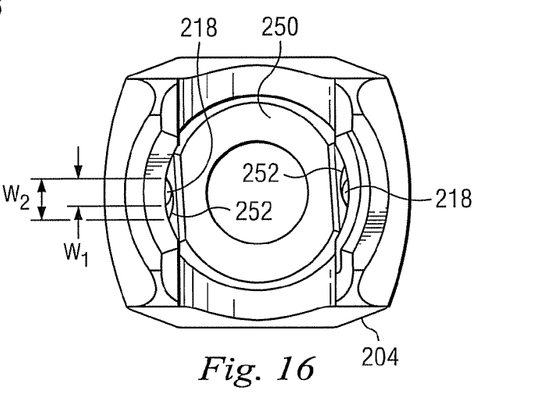
FIGS. 16 and 17 are illustrations of a top view of a coupling assembly including the seat member in FIG. 15.
Figure 17:
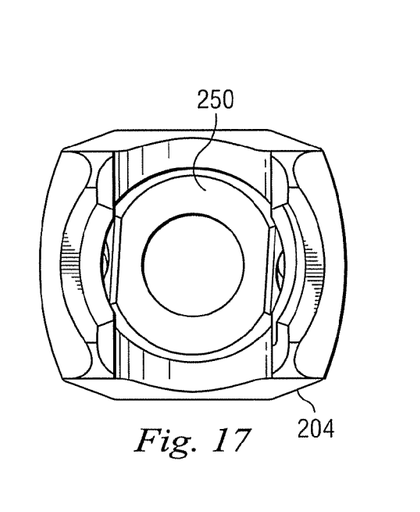

FIGS. 15-17 show an alternate embodiment of a seat member 250 usable with the receiver member 204. FIG. 15 shows the seat member 250 and FIGS. 16 and 17 show a top view of the seat member 250 in the receiver member 204. In this embodiment, the seat member 250 includes a rotation limiting feature 252 that does not have a profile or shape that closely matches the shape of the receiver member's rotation limiting feature 218. As labeled in FIG. 16, the seat member's rotation limiting feature 252 has a width W2 greater than a width W1 of the receiver member's rotation limiting feature 218. Accordingly, as seen in FIGS. 16 and 17, the seat member 250 is allowed some degree of rotation within the receiver member 206, but is limited from exceeding a desired amount of rotation. FIG. 16 shows the seat member 250 rotated to one extreme in a first direction, and FIG. 17 shows the seat member 250 rotated to one extreme in an opposite direction. This may allow the seat member to adjust slightly to align with an implant, but still securely limits the rotation so that the seat member is maintained in a proper alignment with the receiver member. In some embodiments, the rotation limiting feature 252 is configured to allow the seat member 250 to rotate within a range of 0 to 20 degrees. In yet other embodiments, the rotation limiting feature 252 is configured to allow the seat member 250 to rotate within a range of 0 to 10 degrees or 0 to 5 degrees. Other ranges, both larger and smaller, are contemplated.

Figure 18:
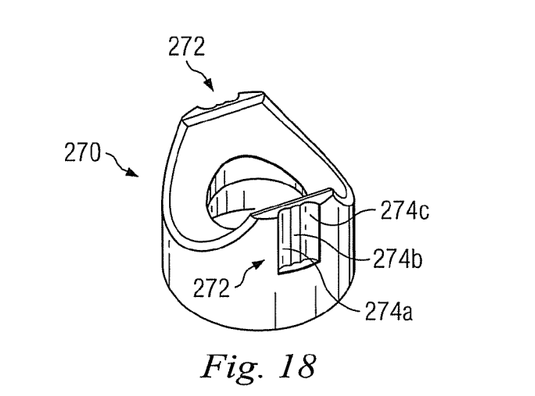
FIG. 18 is an illustration of an isometric view of another exemplary seat member.
Figure 19:
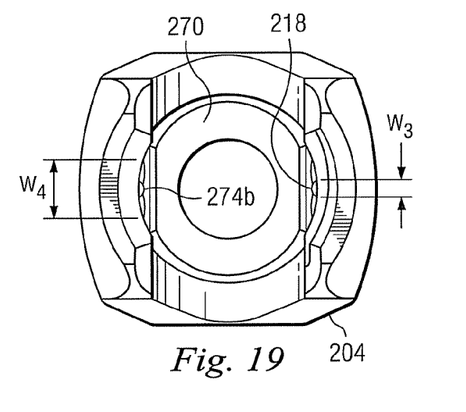
FIGS. 19 and 20 are illustrations of a top view of a coupling assembly including the seat member in FIG. 18.
Figure 20:
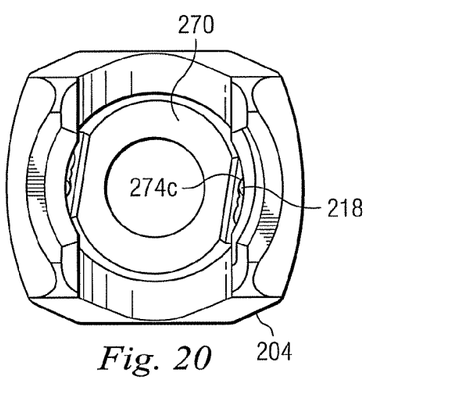

FIGS. 18-20 show another alternate embodiment of a seat member 270 usable with the receiver member 204. FIG. 18 shows the seat member 270 and FIGS. 19 and 20 show the seat member 270 in the receiver member 204. Referring to FIG. 18, the seat member 270 includes a rotation limiting feature 272 that does not have a profile or shape that closely matches the shape of the receiver member's rotation limiting feature 218. As labeled in FIG. 19, the seat member's rotation limiting feature 272 has a width W4 greater than a width W3 of the receiver member's rotation limiting feature 218. In this embodiment, the seat member's rotation limiting feature 272 is a multi-position feature that mates with the receiver member's rotation limiting feature 218 in more than one position. In the embodiment shown, the multi-position feature is a plurality of adjacent grooves 274a-c forming a scallop-like surface. These grooves 274a-c are each configured to receive the receiver member's rotation limiting feature 218 and may be shaped to slidably fit at least a part, such as an outermost end, of the rotation limiting feature 218. In the embodiment shown, the rotation limiting feature includes three grooves providing three positions for the seat member 270 inside the receiver member 204. Accordingly, the seat member 270 is configured to fit at a particular desired position of rotation within the receiver member 206.

FIG. 19 shows the seat member 270 in a straight or neutral position. Accordingly, the receiver member's rotation limiting feature 218 is fit within the center groove 274b. FIG. 20 shows the seat member 270 off-center with the receiver member's rotation limiting feature 218 in groove 274c. This may allow an implanting physician to orient the seat member 270 to a desired position within the receiver member 204, and still substantially restrict rotation of the seat member within the receiver member 204. In some embodiments, the grooves 274a-c of the rotation limiting feature 272 are spaced to provide incremental rotational positioning every 0.25 to 2 degrees. In yet other embodiments, the grooves 274a-c are spaced to provide incremental rotational positioning every 0.25 to 5 degrees. Other increments, both larger and smaller, are contemplated. In some alternate embodiments, the grooves are spaced from each other, with each groove forming an independent groove, rather than being adjacent to each other. Other types of incremental features are also contemplated.

Figure 23:
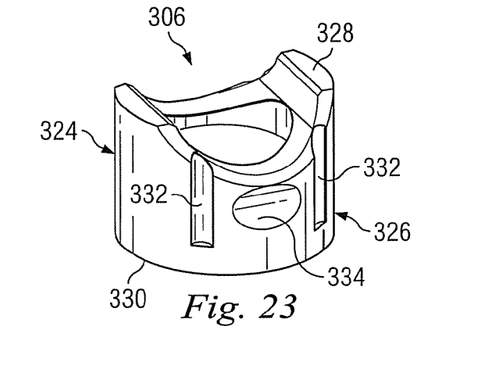
FIG. 23 is an illustration of an isometric view of an exemplary seat member of the coupling assembly of FIG. 21.

FIGS. 21-27 show yet another embodiment of a coupling system 300. As with the coupling system 200, the differences will be described while some similar features will not be again described. Referring to FIG. 23, the coupling system 300 includes an anchor member (not shown) a receiver member 304, a seat member 306, a securing member (not shown), and a rotation limiter 310.

Figures 21, 22:
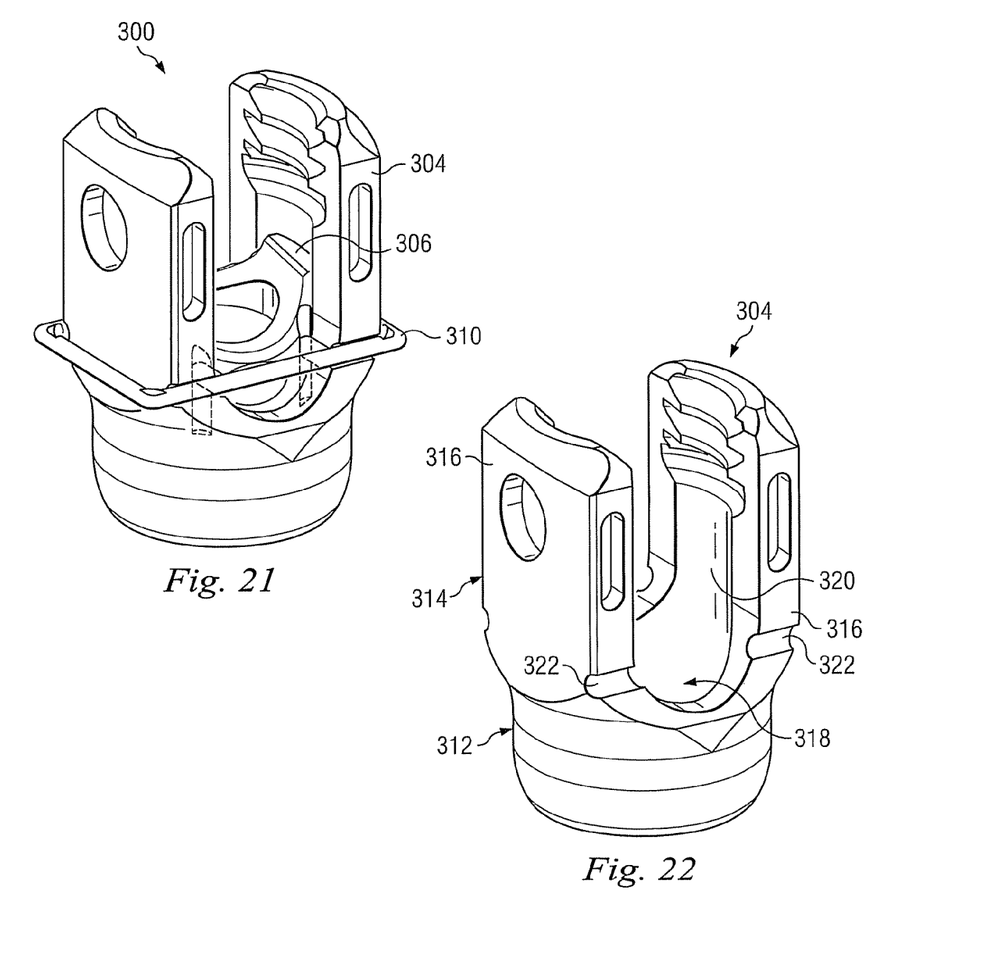
FIG. 21 is an illustration of an isometric view of another exemplary coupling assembly without a securing member or an anchor member.
FIG. 22 is an illustration of an isometric view of an exemplary receiver member of the coupling assembly of FIG. 21.

The receiver member 304 in FIG. 22 includes a lower portion 312 and an upper portion 314. A pair of opposing arms 316 extends axially from opposite sides of the lower portion 312. The opposing arms 316 define an implant receiving aperture 318 therebetween that is sized to receive an implant, such as the implant 110 in FIG. 1. An inner surface 320 extends through the lower and upper portions 312, 314. In the embodiment shown, the inner surface 320 is a smooth cylindrical surface void of rotation limiting features.

The upper portion 314 includes at least one rotation limiting feature 322 formed on an exterior of the receiver member 304. In the embodiment shown, the rotation limiting feature 322 is a groove extending along the arms 316 near the lower portion 312 and adjacent the implant receiving aperture 318. In other embodiments, the rotation limiting feature 322 is protrusion or other surface feature.

Figure 24:
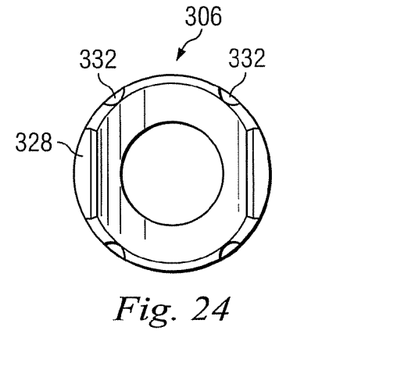
FIG. 24 is an illustration of a top view of the seat member of FIG. 23.
Figure 26:
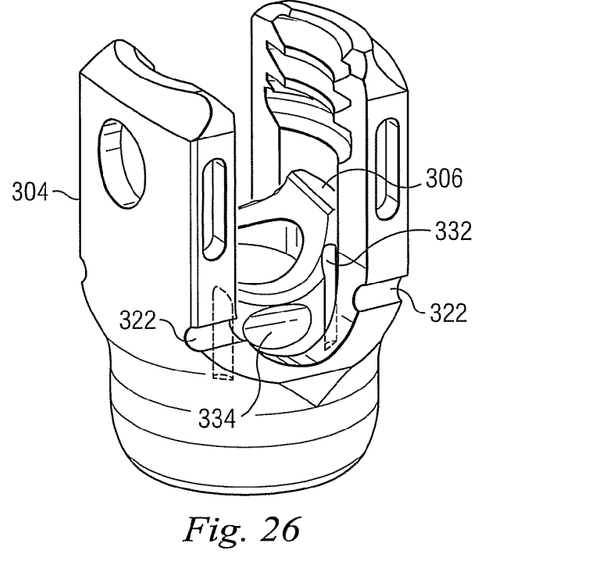
FIG. 26 is an illustration of the coupling assembly of FIG. 21 without the rotation limiter.

The seat member 306, seen best in FIGS. 23 and 24, includes a cylindrical upper portion 324 and a lower portion 326. The upper portion 324 includes an upper end 328 and the lower portion 326 includes a lower end 330. The upper end 328 may include the implant support surface. The upper portion 324 also includes an axial rotation limiting feature 332, which in this embodiment, is a groove extending from the upper end 328 toward the lower end 330, ending at the lower portion 326. A transverse rotation limiting feature 334 is also formed in the seat member along the upper portion 324. The transverse rotation limiting feature 334 here is a transverse groove formed in the cylindrical outer surface of the seat member 306, and may be used simultaneously with the axial rotation limiting feature 332 to limit rotation, or alternatively, may simply provide clearance along the edge of the seat member 306. As best seen in FIG. 26, when disposed within the receiver member 304, the seat member's rotation limiting features 332, 334 do not relate with or engage the receiver member's rotation limiting feature 322.

Figure 25:
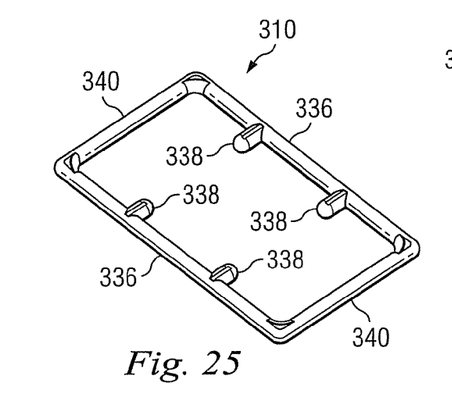
FIG. 25 is an illustration of a rotation limiter of the coupling assembly of FIG. 21.

The rotation limiter 310 best seen in FIG. 25 is configured to engage the rotation limiting features on both the receiver member 304 and the seat member 306 and limit the rotation of the seat member 306 within the receiver member 304. In the embodiment shown in FIG. 25, the rotation limiter is a snap ring having rails 336 and projecting nubs 338. The rails 336 may be configured to engage the receiver member 304 and the projecting nubs 338 may be configured to engage the seat member 306. Connection pieces 340 may connect the rails 336 at ends, forming a closed body. It should be noted that the rails 336 also may interface with the seat member 306, and in the embodiment shown, also interface with the transverse rotation limiting feature 334. In other embodiments, the rails interface only with the receiver member 304.

Figure 27:
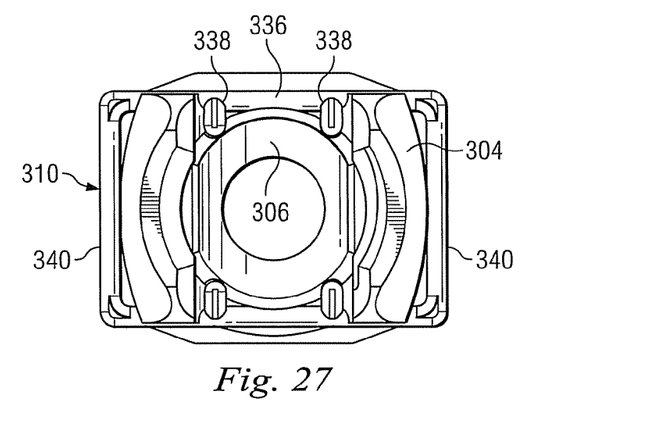
FIG. 27 is an illustration of a top view of the coupling assembly of FIG. 21.

Referring now to FIGS. 21 and 27, the exemplary rotation limiter 310 is configured to extend about the exterior or periphery of the receiver member 304. The rotation limiting features 322 receive and secure the rails 336 in place along the exterior of the receiver member 304. The nubs 338 protrude through the implant receiving aperture 318 to engage the seat member's axial rotation limiting features 332. In addition, in the embodiment shown, the seat member's transverse rotation limiting feature 334 may engage with the rail 336, or alternatively, may provide clearance for the rail 336. During assembly and implantation, the seat member 306 is placed into the receiver member 304. Although the anchor member limits movement in one axial direction, the seat member both may rotate and may axially travel in the other direction. The rotation limiter 310 is placed over the receiver member to engage the rotation limiting features 322, 332, 334 on both the receiver member 304 and the seat member 306, and thereby limit the rotation and limit the axial movement of the seat member 306 relative to the receiver member 304. The transverse rotation limiting feature 334 may have width sufficient to still allow axial sliding relative to the rail 336 of the motion limiter 310. Once secured in place, in some embodiments, the rotation limiter 310 is removed, as the implant frictionally secures the seat member 306 in place relative to the receiver member 304.

It should be understood that in alternative embodiments, the rotation limiting features described on the seat members may be formed on the receiver members and that the rotation limiting features described on the receiver members may be formed on the seat members. Also, in embodiments employing a rotation limiter, the rotation limiter need not extend entirely about the exterior of the receiver member and in some embodiments, the receiver member or the seat member may not include all the disclosed rotation limiting features, including, for example, the transverse rotation limiting feature.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

We claim:

1. A coupling assembly for coupling to an implant having a longitudinal axis, comprising:
   an anchor member;
   a receiver member having an anchor member end that cooperates with the anchor member and having an implant receiving aperture for receiving an implant, the receiver member having a shaped inner surface forming a first rotation-limiting feature; and
   a seat member disposable within the receiver member between the anchor member and the implant receiving aperture, the seat member including a first outer surface portion and a second outer surface portion, the first outer surface portion having a circular perimeter and the second outer surface portion having a non-circular perimeter, the second outer surface portion forming a second rotation-limiting feature, the second rotation-limiting feature having a length and a width, the length being greater than the width, the seat member being arranged so that the length extends in the direction of the longitudinal axis of an implant carried by the seat member, and the seat member being arranged so that the width is transverse to the direction of the longitudinal axis of the implant, the first and second rotation-limiting features being engageable to limit rotation of the seat member relative to the receiver member,
   wherein the seat member includes a shoulder formed between the circular perimeter of the first outer surface portion and the non-circular perimeter of the outer second surface portion, the shoulder being configured to engage the receiver member and limit axial travel of the seat member within the receiver member.

2. The coupling assembly of claim 1, wherein the seat member is disposable within the receiver member through the anchor member end.

3. The coupling assembly of claim 1, wherein the shaped inner surface and the shaped second outer surface portion are oval shaped surfaces.

4. The coupling assembly of claim 1, wherein the seat member is configured to axially slide within the receiver member when the first and second rotation-limiting features are engaged.

5. The coupling assembly of claim 1, wherein the inner surface of the receiver member includes a surface portion having a circular inner surface portion and having a non-circular inner surface portion forming the shaped inner surface.

6. The coupling assembly of claim 5, wherein the non-circular perimeter of the seat member and the non-circular inner surface portion of the receiver member are smooth surfaces.

7. The coupling assembly of claim 1, wherein a transverse cross-section of the seat member includes a length greater than a width.

8. The coupling assembly of claim 7, wherein the length of the seat member is configured to align with an axis of the implant.

9. The coupling assembly of claim 1, wherein the seat member includes an implant support surface that partially defines the implant receiving aperture, the implant support surface having a bull nose surface portion extending to a perimeter surface of the seat member.

10. The coupling assembly of claim 9, wherein the perimeter surface of the seat member is the second outer surface portion.

11. The coupling assembly of claim 1, including a securing member configured to cooperate with the receiver member to secure the implant within the implant receiving aperture, the securing member having a distal implant engaging portion mounted thereon.

12. The coupling assembly of claim 1, including a securing member configured to cooperate with the receiver member to secure the implant within the implant receiving aperture, the securing member being having a break-off portion.

13. The coupling assembly of claim 1, wherein the seat member includes a perimeter surface and an implant support surface that partially defines the implant receiving aperture, the implant support surface and perimeter surface forming an edge extending about seat member, the edge having a substantially constant radius of curvature.

14. The coupling assembly of claim 13, wherein the perimeter surface of the seat member is the second outer surface portion.

15. A coupling assembly for coupling to an implant having a longitudinal axis, comprising:
   an anchor member;
   a receiver member having an anchor member end cooperating with the anchor member and having an implant receiving aperture for receiving an implant, the receiver member having an annular inner surface portion;
   a seat member disposable within the receiver member between the anchor member and the implant receiving aperture, the seat member including a first outer surface portion and a second outer surface portion, the first outer surface portion having a circular perimeter and the second outer surface portion having a non-circular, annular outer peripheral surface portion, the non-circular, annular outer peripheral surface portion defining a seat surface having a length and a width, the length being greater than the width, the seat member being arranged so that the length extends in the direction of the longitudinal axis of an implant carried by the seat member, and the seat member being arranged so that the width is transverse to the direction of the longitudinal axis of the implant, the annular inner surface portion and the non-circular, annular outer peripheral surface portion being engageable to limit rotation of the seat member relative to the receiver member,
   wherein the seat member includes a shoulder formed between the circular perimeter of the first outer surface portion and the non-circular, annular outer peripheral surface portion of the outer second surface portion, the shoulder being configured to engage the receiver and limit axial travel of the seat member within the receiver member in the direction toward the implant receiving aperture.

16. The coupling assembly of claim 15, wherein the seat member is disposable within the receiver member through the anchor member end.

17. The coupling assembly of claim 15, wherein the annular inner surface portion and the annular outer peripheral surface portion surface are oval shaped.

18. The coupling assembly of claim 15, wherein the seat member is axially slidable within the receiver member when the annular inner surface portion and the annular outer peripheral surface portion are engaged.

19. The coupling assembly of claim 15, wherein a transverse cross-section of the seat member includes a length greater than a width, the length being configured to align with an axis of the implant.

20. A method of assembling a coupling assembly for securing an implant having a longitudinal axis, comprising:
  introducing a seat member into a receiver member having an anchor member end configured to cooperate with an anchor member and having an implant receiving aperture for receiving an implant, wherein introducing the seat member includes introducing the seat member into the anchor member end so that a shoulder on the seat member engages an internal shoulder on the receiver member and limits axial travel of the seat member within the receiver member, the shoulder on the seat member being formed between a first outer surface portion of the seat member having a first perimeter dimension and a second outer surface portion of the seat member having a second perimeter dimension larger than the first perimeter dimension; and
  limiting rotation of the seat member relative to the receiver member by engaging a shaped inner surface of the receiver member forming a first rotation-limiting feature with the second outer surface portion of the seat member forming a second rotation-limiting feature the second rotation-limiting feature having a length and a width, the length being greater than the width, the seat member being arranged so that the length extends in the direction of the longitudinal axis of an implant carried by the seat member, and the seat member being arranged so that the width is transverse to the direction of the longitudinal axis of the implant.

21. The method of claim 20, including introducing an anchor member into the anchor member end of the receiver member so that the seat member is disposed between the anchor member and the implant receiving aperture.

22. The method of claim 20, wherein the introducing the seat member includes introducing the seat member into the anchor member end of the receiver member.

23. The method of claim 20, wherein the engaging a shaped inner surface of the receiver member with a shaped outer surface of the seat member includes engaging a first oval shaped surface with a second oval shaped surface.

24. The method of claim 20, including permitting the seat member to axially slide within the receiver member while the first and second rotation-limiting features are engaged.

25. A coupling assembly for coupling to an implant having a longitudinal axis, comprising:
  an anchor member;
  a receiver member having an anchor member end that cooperates with the anchor member and an implant receiving aperture for receiving an implant, the receiver member including an inner surface and a first rotation-limiting feature associated with the inner surface; and
  a seat member disposable within the receiver member between the anchor member and the implant receiving aperture, the seat member including a first outer surface portion and a second outer surface portion, the first outer surface portion having a circular perimeter and the second outer surface portion having a non-circular perimeter, the second outer surface portion forming a second rotation-limiting feature, the second rotation-limiting feature having a length and a width, the length being greater than the width, the seat member being arranged so that the length extends in the direction of the longitudinal axis of an implant carried by the seat member, and the seat member being arranged so that the width is transverse to the direction of the longitudinal axis of the implant, and
  wherein one of the first and second rotation limiting features is sized with a width greater than a width of the other of the first and second rotation limiting features, the first and second rotation-limiting features being engageable to limit rotation of the seat member relative to the receiver member, and
  wherein the seat member includes a shoulder formed between the circular perimeter of the first outer surface portion and the non-circular perimeter of the outer second surface portion, wherein the shoulder is configured to engage the receiver and limit axial travel of the seat member within the receiver member.

26. The coupling assembly of claim 25, wherein the one of the first and second rotation limiting features sized with the greater width includes a plurality of positions is shaped to selectively cooperate with the other of the first and second rotation limiting features having the lesser width to limit rotation of the seat member relative to the receiver member.

27. The coupling assembly of claim 25, wherein the one of the first and second rotation limiting features sized with the greater width is a groove having a smooth surface shaped to selectively cooperate with the other of the first and second rotation limiting features having the lesser width to limit rotation of the seat member relative to the receiver member.

28. A coupling assembly for coupling to an implant having a longitudinal axis, comprising:
  an anchor member;
  a receiver member having an anchor member end that cooperates with the anchor member and an implant receiving aperture for receiving an implant, the receiver member including an inner surface and a first rotation-limiting feature associated with the inner surface; and
  a seat member disposable within the receiver member between the anchor member and the implant receiving aperture, the seat member including a first outer surface portion and a second outer surface portion, the first outer surface portion having a circular perimeter and the second outer surface portion having a non-circular perimeter, the second outer surface portion forming a second rotation-limiting feature associated with the outer surface, the second rotation-limiting feature having a length and a width, the length being greater than the width, the seat member being arranged so that the length extends in the direction of the longitudinal axis of an implant carried by the seat member, and the seat member being arranged so that the width is transverse to the direction of the longitudinal axis of the implant,
  the first and second rotation-limiting features being engageable to permit a limited degree of rotation of the seat member relative to the implant receiver member,
  wherein the seat member includes a shoulder formed between the circular perimeter of the first outer surface portion and the non-circular perimeter of the outer second surface portion, wherein the shoulder is configured to engage the receiver and limit axial travel of the seat member within the receiver member.

* * * * *